(12) United States Patent
Harris

(10) Patent No.: US 6,248,132 B1
(45) Date of Patent: Jun. 19, 2001

(54) HIP REPLACEMENT PROSTHESIS

(76) Inventor: Charles C. Harris, 8206 W. Planada La., Peoria, AZ (US) 85382

( * ) Notice: Subject to any disclaimer, the term of this patent is extended or adjusted under 35 U.S.C. 154(b) by 0 days.

(21) Appl. No.: 09/431,555

(22) Filed: Oct. 29, 1999

(51) Int. Cl.$^7$ .................................................. A61F 2/32
(52) U.S. Cl. ............................................... 623/22.15
(58) Field of Search ...................... 623/22.14, 22.15, 623/22.17, 22.18, 22.19, 22.24, 22.25, 22.28, 22.31, 22.39, 22.4, 22.42, 23.15, 23.21, 23.23, 23.24, 22, 23, 18

(56) References Cited

U.S. PATENT DOCUMENTS

| Re. 31,865 | * | 4/1985 | Roux ................................ 623/22.29 |
| 3,813,699 | * | 6/1974 | Giliberty ......................... 623/22.17 |
| 4,021,865 | * | 5/1977 | Charnley ......................... 623/23.24 |
| 4,159,544 | * | 7/1979 | Termanini ........................ 623/22.14 |
| 4,180,873 | * | 1/1980 | Fixel ............................... 623/22.23 |
| 4,563,778 | * | 1/1986 | Roche, et al. ................... 623/22.38 |
| 4,728,335 | * | 3/1988 | Jurgutis ........................... 623/23.23 |
| 4,795,471 | * | 1/1989 | Oh .................................. 623/22.19 |
| 4,960,427 | * | 10/1990 | Noiles ............................. 623/22.18 |
| 5,080,678 | * | 1/1992 | Spotorno et al. ............... 623/22.14 |
| 5,824,108 | * | 10/1998 | Huebner .......................... 623/22.29 |

FOREIGN PATENT DOCUMENTS

2069338 * 8/1981 (GB) ............................. 623/22.15

* cited by examiner

Primary Examiner—Jeffrey A. Smith
Assistant Examiner—Eduardo C. Robert
(74) Attorney, Agent, or Firm—Cohn, Powell & Hind

(57) ABSTRACT

A hip joint prosthesis including a stem assembly attached to the femur and having a generally spherical head and a cup assembly having an outer casing received within the hip socket. The cup assembly outer casing includes threadedly attached upper and lower portions to encapsulate the lining and the lining includes an upper portion having a recess receiving the head and a split lower portion seating the head. The cup assembly also includes an interior spring assembly providing shock absorption between the head and the casing. The stem assembly includes an elongate stem and a cooperating shield attached to the stem, the stem being independently movable following insertion of the stem and shield into the femur.

20 Claims, 5 Drawing Sheets

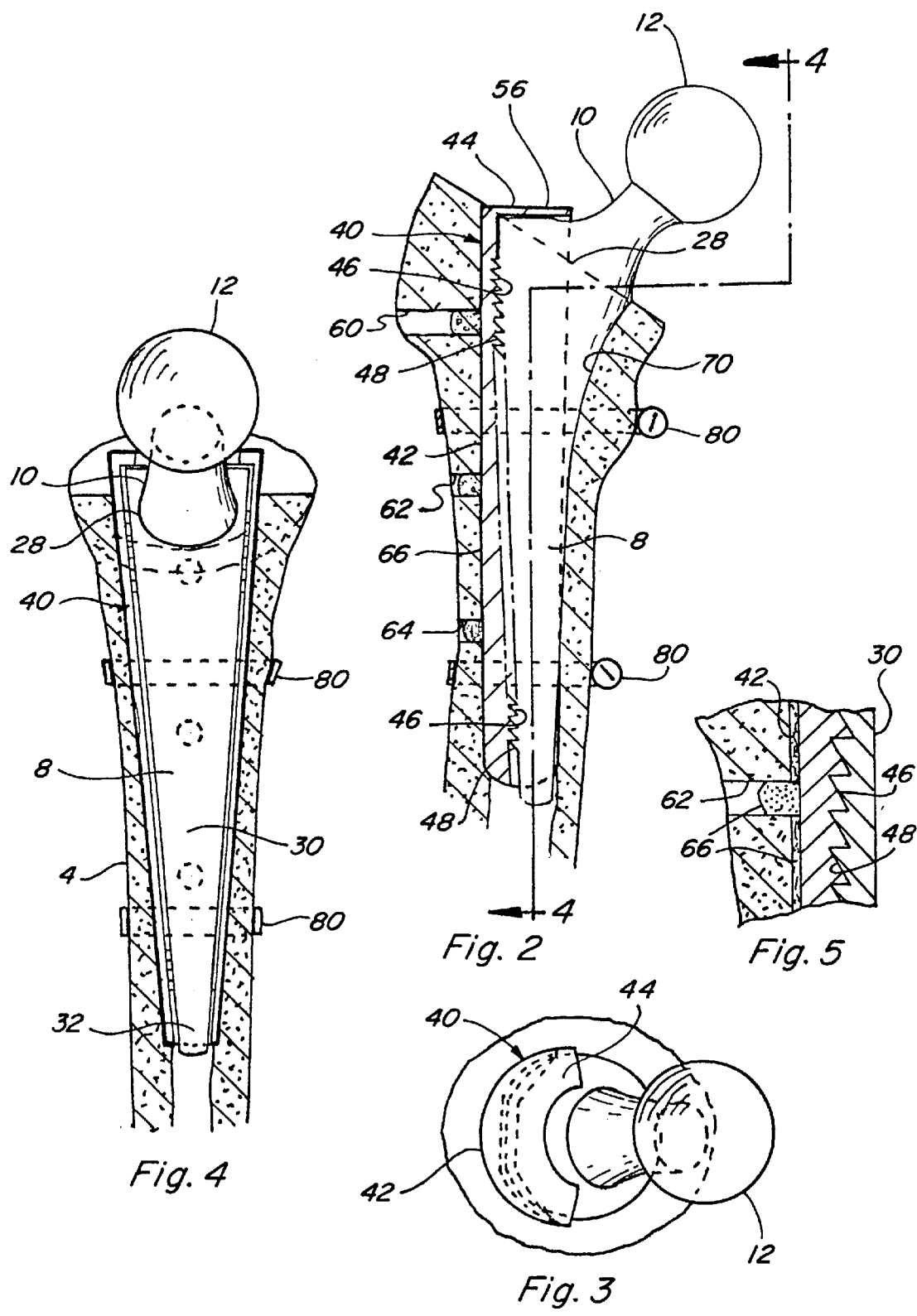

HIP REPLACEMENT PROSTHESIS

BACKGROUND OF THE INVENTION

This invention relates generally to artificial joints and particularly to an endoprosthesis for the hip joint.

Artificial joints and especially those for the hip have been known for many years. Such replacement devices include substitute members for the two parts of the natural joint, namely, the femoral head, which is joined to the femur, and the hip socket which receives and cooperates with the head to provide a natural universal joint.

Replacement of the natural hip joint parts is necessary when deterioration has occurred to one or both of the natural femoral head and socket. Ideally, the replacement members should reproduce the structure and function of the members which they replace. It is important that the femoral head be securely attached to the femur, that the head be received within the socket and that the resulting joint be produced with a degree of resilience or cushioning.

U.S. Pat. No. 4,770,661 discloses a replacement joint having a cup assembly which includes a generally hemispherical metal outer shell threaded at the rim and having an upper part received directly into the hip socket; an interfitting plastic core received within the shell and a split plastic locking ring. The core in turn receives the femoral head and the split plastic locking ring is installed by attaching the plastic parts under the head, cementing the parts together and then threadedly locking the plastic parts to the metal outer shell thereby encapsulating the ball. There is no metal casing encapsulating the head but rather a combined plastic and metal casing. Also lacking is any resilient feature between the head and the socket. U.S. Pat. No. 4,159,544 discloses an exterior spring system between the head and the socket. U.S. Pat. No. 3,648,294 discloses an arrangement which provides a rather complicated piston and cylinder construction within the head. U.S. Pat. No. 4,406,023 discloses the use of a lubricant filled bellows system for providing joint resilience. U.S. Pat. No. 4,199,824 discloses a femoral prosthesis having a flange and serrations to provide additional support and load transfer capability between the joint parts. All five of these prior patents are incorporated herein by reference.

The present hip joint replacement represents an improvement over prior art devices and overcomes problems and provides advantages in a manner not revealed in the known prior art.

SUMMARY OF THE INVENTION

This invention provides an artificial hip joint replacement which provides substantially universal joint movement between a stem assembly which is secured to the hollowed out passage of the femur and a cup assembly, which relatively receives the femoral head and is itself rotatively received within the prepared hip socket, said socket being fitted with a firmly attached socket shell.

The structural arrangement of parts provides for rotational movement of the cup assembly about the radial center of the socket and pivotal movement of the stem about the center of the femoral head and circular movement of the head about the axis of the femoral neck.

The hip joint prosthesis provides a stem assembly attached to the femur including a generally spherical head and a cup assembly having an outer casing received with the socket and an inner lining receiving the head.

It is an aspect of this invention to provide that the cup assembly outer casing includes an upper portion and a lower portion threadedly attached to the upper portion to encapsulate the lining, the lining including an upper portion received within the casing upper portion and having a recess receiving the head, said lining having a lower portion received within the casing lower portion and having a recess seating the head, said lining lower portion being split into at least two portions surrounding the head.

It is another aspect of this invention to provide that the cup assembly includes resilient means therewithin providing shock absorption between the head and the casing.

It is another aspect of this invention to provide that the stem assembly includes an elongated stem and a shield and means between the stem and the shield permitting independent movement of the stem relative to the shield following insertion of the stem and shield together in an elongate passage into the femur.

This invention provides a hip replacement which is relatively inexpensive, easy to manufacture and install and efficient in providing natural joint movement.

BRIEF DESCRIPTION OF THE DRAWINGS

FIG. 2 is a sectional view of the stem assembly;

FIG. 3 is a plan view thereof;

FIG. 4 is a sectional view taken on Line 4—4 of FIG. 2;

FIG. 5 is an enlarged simplified detail showing the connection between the stem assembly body and shield;

DESCRIPTION OF THE PREFERRED EMBODIMENT

Figure 1:
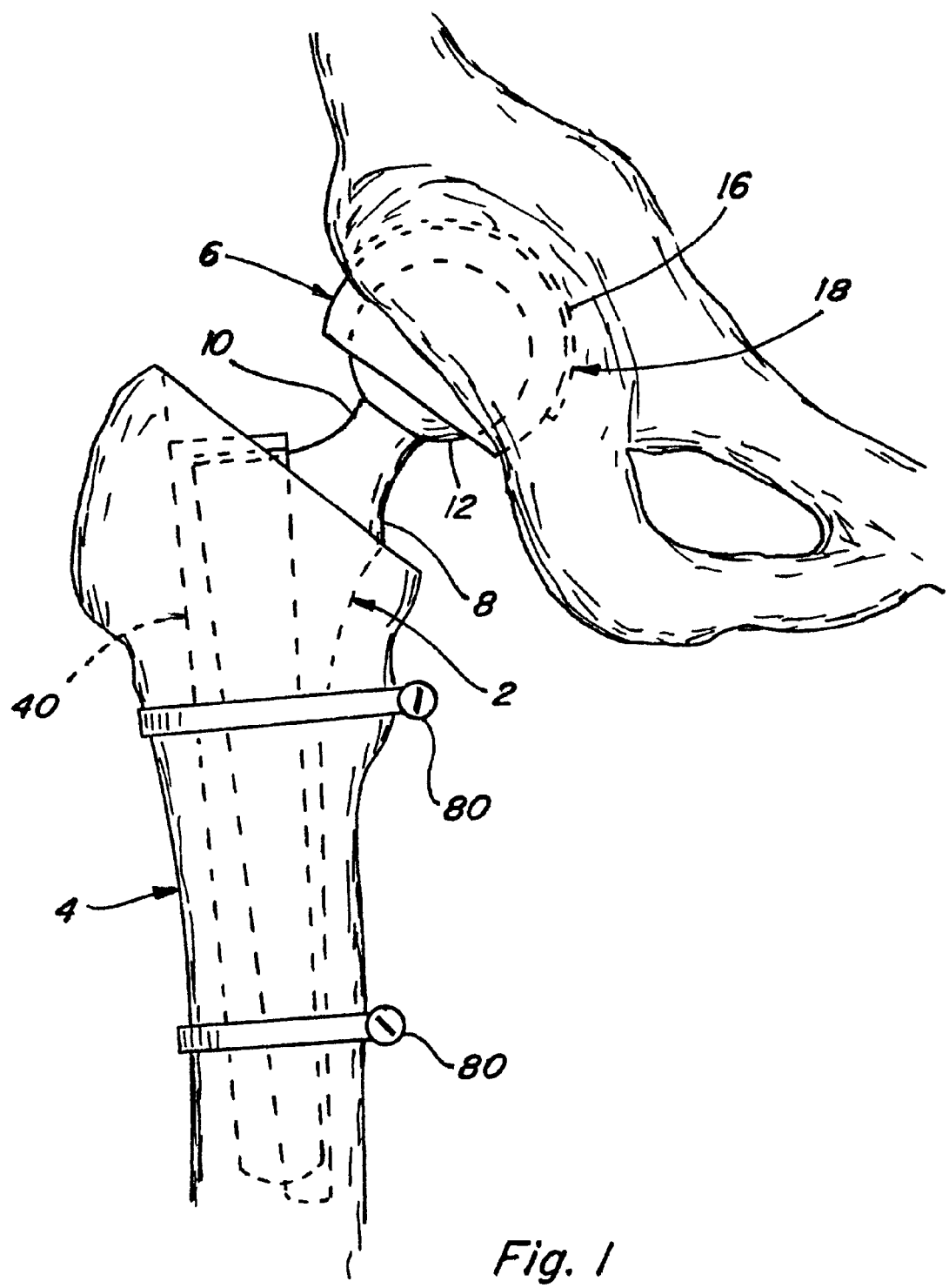
FIG. 1 is an elevational view of the hip prosthesis as installed.

Referring now by reference numerals to the drawings and first to FIG. 1, the hip joint prosthesis 1 includes a stem assembly 2 secured within a femur 4 and a cup assembly 6 rotatably connected to the associated hip socket 18. The stem assembly 2 includes an elongated metal stem 8, a neck 10, and a generally spherical head 12. The spherical head 12 is encapsulated within the cup assembly 6, the cup assembly 6 rotating freely within a generally spherical metal socket shell 16 cemented within the hip socket 18.

Figures 6, 7:
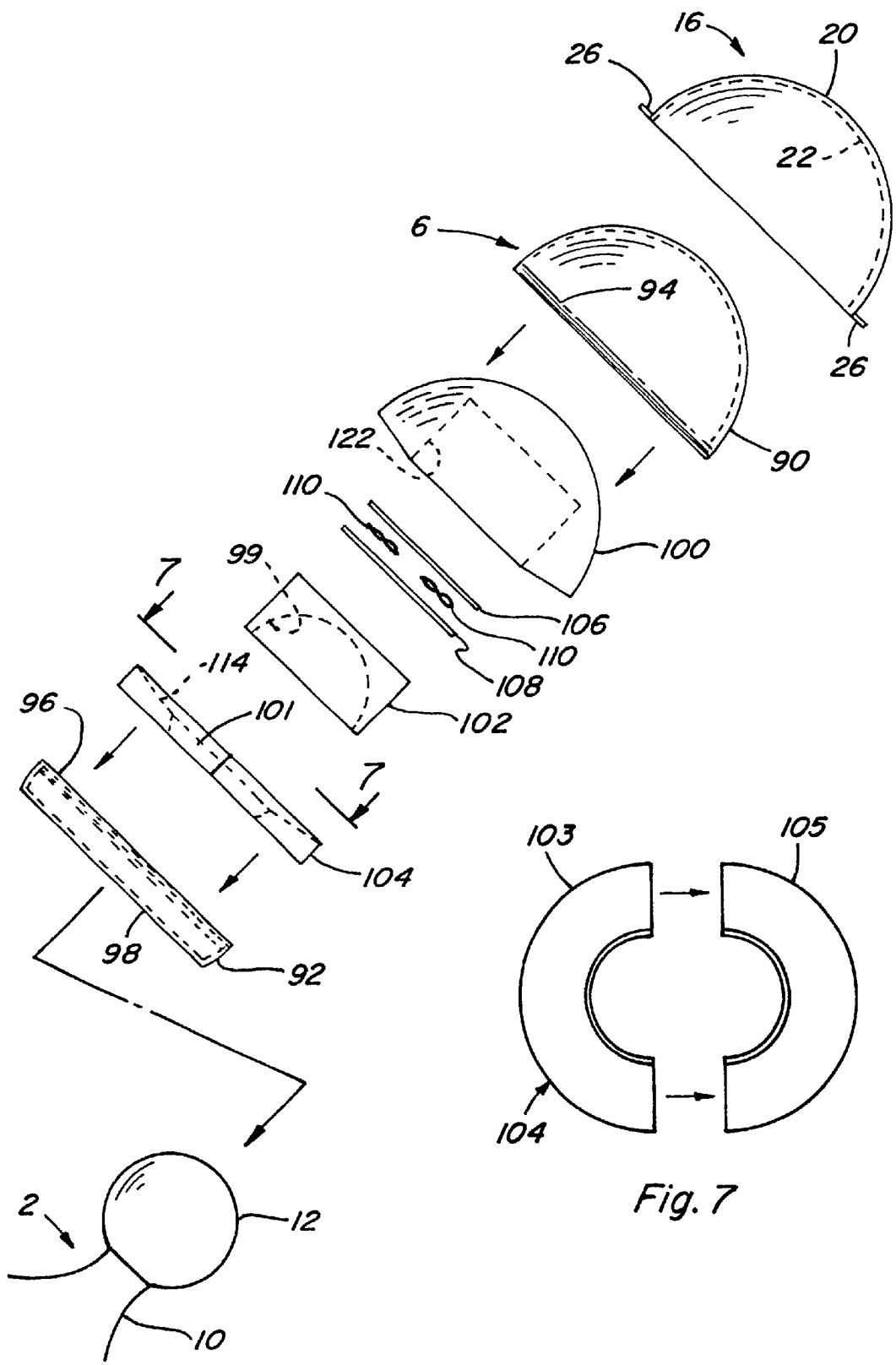
FIG. 6 is an exploded view of the cap assembly.
FIG. 7 is a plan view of the split liner portions taken on Line 7—7 of FIG. 6.
Figure 8:
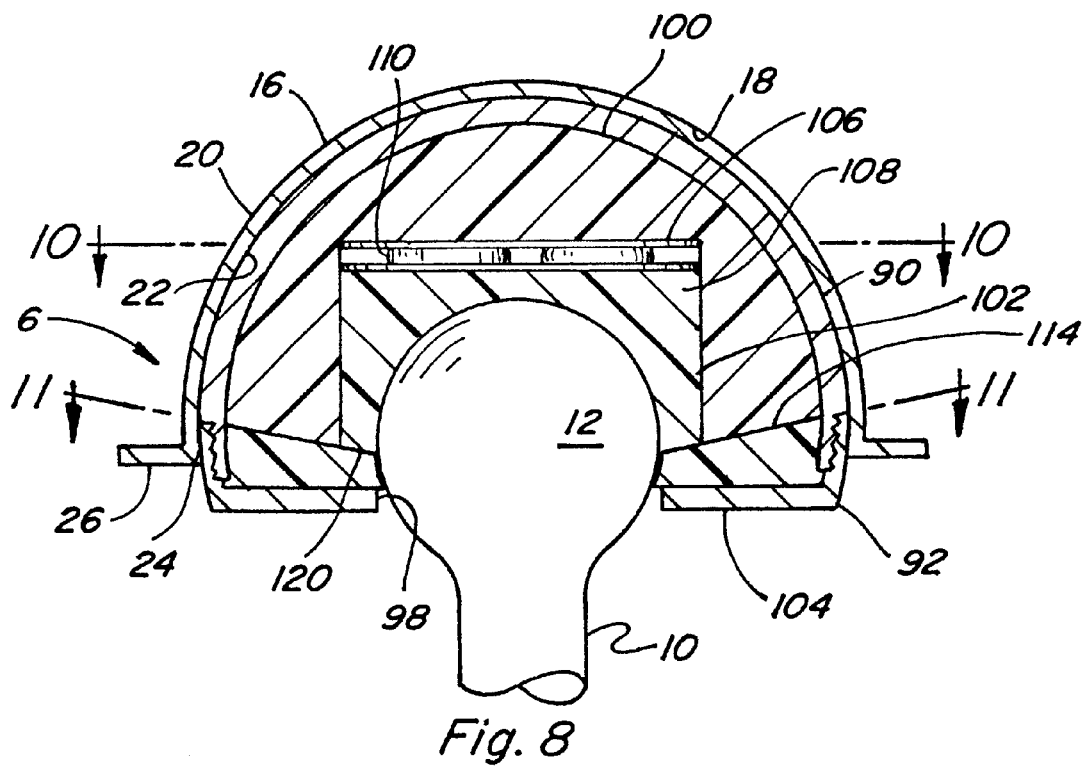
FIG. 8 is an enlarged sectional view of the cup assembly parts as installed.
Figure 9:
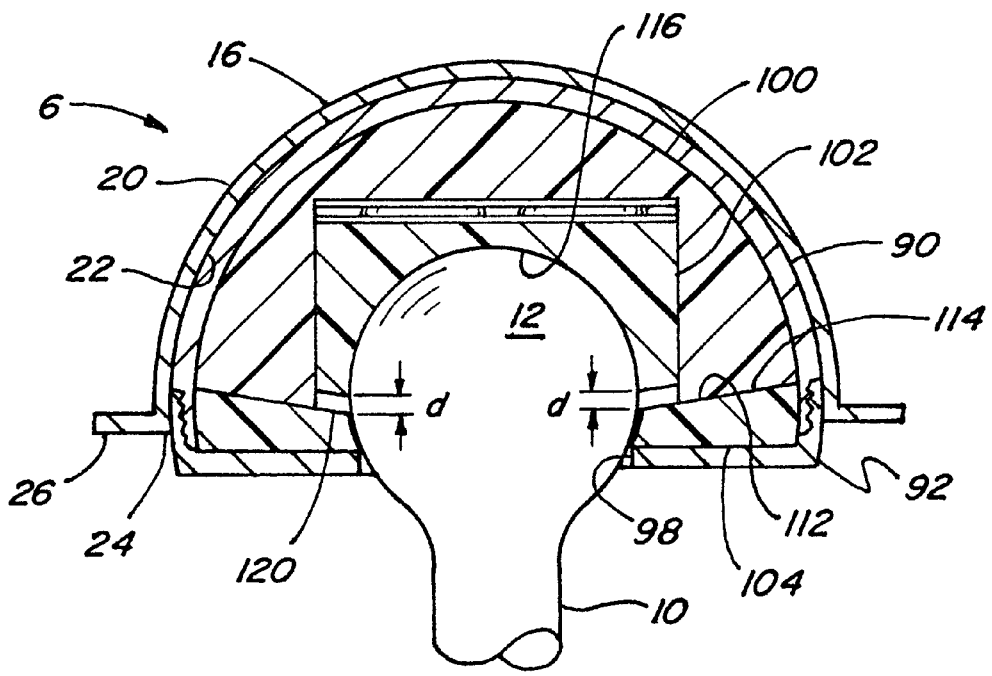
FIG. 9 is a similar view to FIG. 8 illustrating the resilient nature of the cup assembly.
Figure 10:
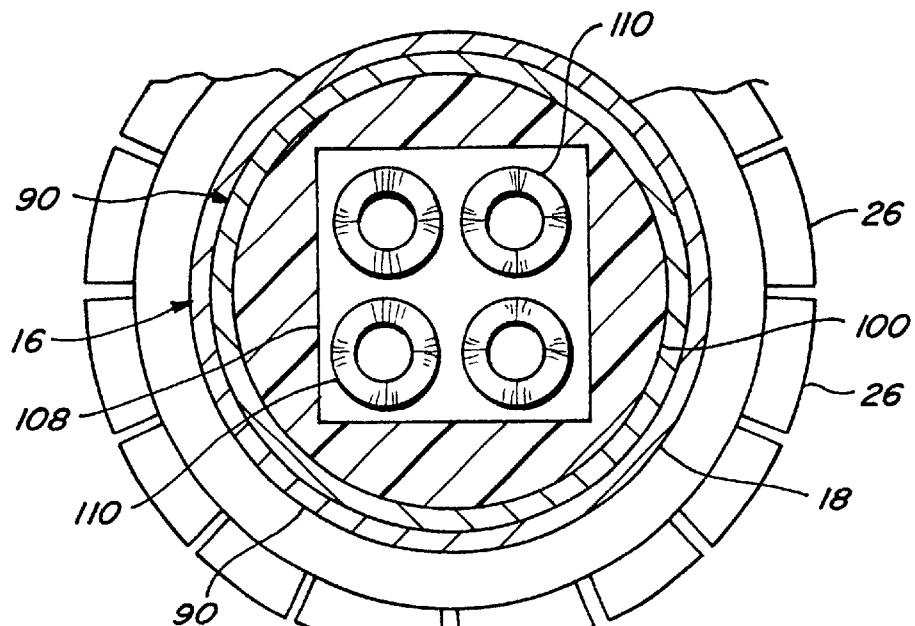
FIG. 10 is a section view taken on Line 9—9 of FIG. 8.
Figure 11:
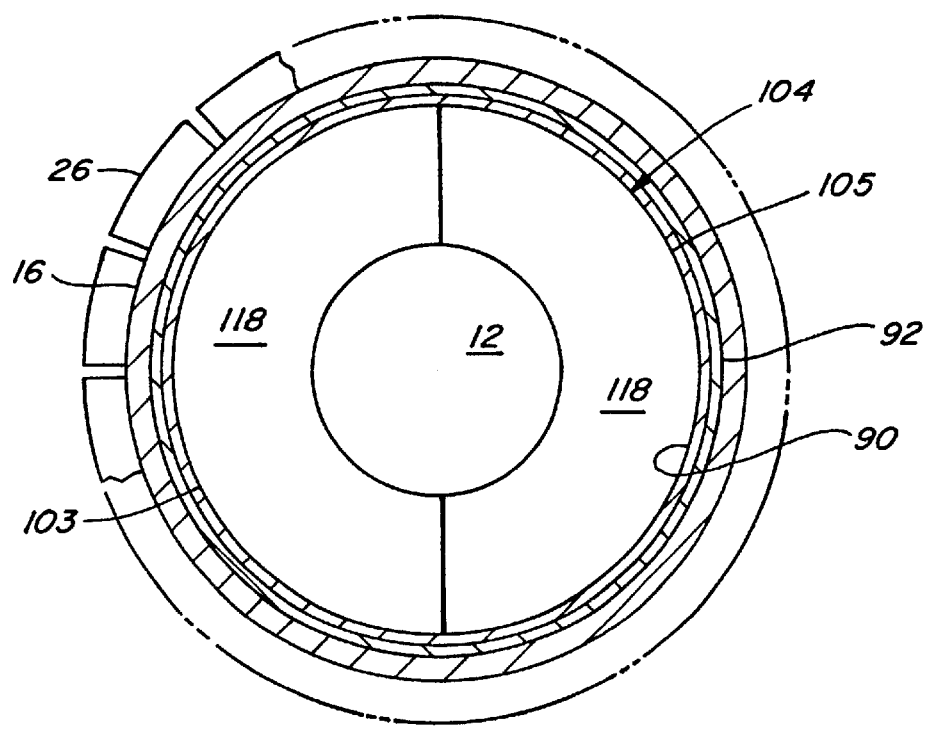
FIG. 11 is a sectional view taken on Line 10—10 of FIG. 8.

Installation of the hip joint prosthesis 1 is briefly as follows: the socket shell 16, as shown in FIGS. 6–8, is first attached to the hip socket 18, then the stem assembly 2, as shown in FIGS. 2–5, is attached to the femur 4, and finally the cup assembly 6 is installed, as shown in FIGS. 6–8, thereby completing the hip joint prosthesis. Provided below are a more detailed description of the structural arrangement of parts and the installation procedure for each of the socket shell 16, the stem-assembly 2, and the cup assembly 6.

FIGS. 2–5 illustrate the attachment of the stem assembly 2 to the femur 4. As shown, the elongated metal stem 8, has an upper shoulder portion 28, unitarily formed with the inwardly directed neck 10 and the head 12 and a tapered body portion 30 which terminates in a lower distal end 32. The cross-section of the lower distal end 32 is relatively narrow, but the cross-section of the tapered body portion 30 gradually increases from the distal end 32 to the shoulder portion 28.

The stem assembly 2 includes a generally L-shaped protective shield 40 having a generally vertical shield back portion 42 and a generally horizontal top portion 44. The vertical inside face of the shield back portion 42 is formed into a plurality of tooth-like triangular steps 46 extending substantially the fill length of said shield. The vertical outside face of the back of the stem body 30 includes corresponding steps 48, which are compatibly shaped to mesh with the shield steps 46, as shown in FIG. 5. The femur 4 includes a predrilled hollowed out passage 70 and a plurality of vertically arranged horizontal openings 60, 62 and 64 communicating with said passage 70. The stem 8 and shield 40 are installed as a unit into said passage 70, the shield only being coated with cement 66. The stem 8 will be held in place by the steps 48 on the shield and steps 46 on the stem 8, as shown in FIG. 5. The shield top portion 44, which is positioned adjacent an abutment 56 of the stem assembly shoulder portion 28, can hammered into place. This allows the cement between the stem and the shield to enter the openings so that when it hardens it will secure the position of the shield in place as shown in FIG. 5. This will allow the stem 8 to move downward when required without the shield moving. Finally, to secure the stem assembly 2 to the femur 4, upper and lower nichrome hose clamps 80, constituting adjustable straps, are attached around the outside of the femur 4 to apply pressure to the outside of said femur, thereby applying inwardly directed pressure to keep the femur 4 from shattering if the femur itself has thinning of the bone walls.

If deterioration of the femur 4 interior causes slippage of the stem body 30 relative to the shield 40, for example by one step, or more, the stem body 30 and the shield 40 will remain tight in femur 4 and no surgery will be needed to reseat the stem as must be done with existing hip prostheses.

FIG. 6 illustrates the arrangement of parts the socket shell 16, which receives the cup assembly 6. As shown, the metal socket shell 16 is hemispherical having an exterior surface 20, a interior surface 22 concentric with its exterior surface 20, and an open circular end defining a rim 24. Surrounding and unitarily formed with the rim 24 are a plurality of outwardly extending tabs 26. During installation, the exterior surface of the socket shell 16 is coated with cement and hammered into the hip socket 18 with the socket shell's open circular end 24 at the bottom of the socket. The outwardly extending tabs 26 help to secure the socket shell 16 to the hip socket 18.

FIGS. 6–11 illustrate the structural arrangement of parts of the cup assembly 6 with greater particularly. As shown, the cup assembly 6 includes upper and lower outer casing portions 90 and 92. The upper casing portion 90 is generally hemispherical and includes a male threaded portion 94 at the rim. The lower casing portion 92, which is generally pan-shaped, constitutes a locking ring, and includes an overlapping matching female threaded portion 96 at the rim, such that the two casing portions 90 and 92, when connected, provide a generally spherical surface, which is received in rotatable relation within the socket shell 16. The lower casing 92 includes an end opening 98, large enough to receive the head 12.

Within the casing formed by threadedly connected portions upper and lower casing portions 90 and 92, respectively, are an upper liner portion 100, having an insert block 102 slidably received within an opening 122 and a lower liner portion 104 which is split into two semi-annular portions 103 and 105.

The upper liner portion 100 and the insert block 102 are spaced from each other at the upper end to form a gap between them occupied by an upper plate 106, a lower plate 108 and a spring means sandwiched between them which, in the embodiment shown, is provided by a plurality of annular wave washers 110. The upper liner portion 100 and the lower split liner portion 104 include interengagable conical surfaces 112 and 114 respectively. Also, the insert block 102 and the lower portion 104, respectively, are formed to receive the spherical surface of the head 12 as indicated by numerals 116 and 118. Also the insert block has a seating surface 120.

The liner portions 100 and 102 are sized to permit the wave spring washers to move axially within the casing, whereby to be compressed to provide the resilience necessary to absorb shock loads. This arrangement is shown by reference to FIGS. 8 and 9 in which the resilient movement is indicated by distance "d", the distance between the moveable insert seating surface 120 and the split liner conical surface 114.

The cap assembly 6 is mounted to the head 12 by preassembling the upper liner portion 100, the plates 106 and 108, with the wave washer 110 therebetween, and the lower split liner portion 104. The casing lower portion 92, which provides a pan-shaped locking ring, can readily be slipped over head 12 and the two split liner portions 103 and 105 may be emplaced within the locking ring on opposite sides of the head 12. The head 12 can then be fitted within the insert block 102 and the lower casing portion 92 locking zing threadedly connected to the upper casing portion 90 to encapsulate the head 12 within the casing.

Finally, to secure the stem-assembly 2 to the femur 4, upper and lower femur adjustable straps 80, preferably ⅜ inch wide Nichrome, are attached around the outside of the femur 4 to apply pressure to the outside 70 urging the outside of the femur 4 inwardly and hold the stem assembly 2 in place within the femur 4.

The step arrangement 46, 48 between the stem body 30 and the shield back portion 42 has the advantage that when the stem 8 descends over time within the femur passage 70, the stem body 30 will move downwardly and engage the next step on the stationary shield 40. During this process, the clamps 80 maintain their pressure on the outside of the femur 4.

With respect to the material from which the hip joint replacement parts are manufactured and formed, the following are preferred. The socket shell 16, and the upper casing portion 90 and lower casing 92 are preferably formed from chrome steel. The inner lining portions, namely, the upper portion 100, the intermediate portion 102 and the split lower portion 104 are preferably formed from hard plastic such as polyethylene. The bearing plates 106 and 108 for the wave washer 110 and the wave washers themselves are preferably formed from stainless steel. The stem assembly head 12 and body 30 are formed from titanium while the expansion shield is formed from stainless steel. Finally, the adjustable hose clamps 80 are formed from nichrome.

It will be understood that ongoing improvements in more exotic materials may suggest alternatives to those suggested above, for example, graphite may be used for in lieu of plastic for the casing lining.

Accordingly, although the hip replacement prosthesis has been described by making detailed reference to a preferred

I claim as my invention:

1. A hip-joint prosthesis adapted to connect a femur and a hip socket, the prosthesis comprising:
   (a) A stem assembly adapted to be attached to the femur and including a generally spherical head; and
   (b) a cup assembly including an outer casing adapted to be received within the socket and an inner lining receiving the head;
   (c) the cup assembly outer casing including an upper portion and a lower portion threadedly attached to the upper portion to completely encapsulate the lining and the lining including an upper portion received within the casing upper portion and having a recess receiving the head and said lining including a lower portion received within the casing lower portion and having a recess seating the head, said lining lower portion being split into at least two portions surrounding the head.

2. A hip joint prosthesis as defined in claim 1, in which:
   (d) the lining upper portion recess receives the head in rotatable relation.

3. A hip joint prosthesis as defined in claim 1, in which:
   (d) said casing lower portion is generally pan-shaped and includes an opening having a diameter large enough to receive the spherical head in clearance relation.

4. A hip joint prosthesis as defined in claim 1, in which:
   (d) the outer casing upper portion includes a rim and the lower portion includes a rim threadedly connected to the upper portion rim to encapsulate the lining.

5. A hip-joint prosthesis adapted to connect a femur and a hip socket, the prosthesis comprising:
   (a) a stem assembly adapted to be attached to the femur and including a generally spherical head; and
   (b) a cup assembly including an outer casing adapted to be received within the socket and an inner lining receiving the head;
   c) the cup assembly outer casing including an upper portion and a lower portion threadedly attached to the upper portion to encapsulate the lining and the lining including an upper portion received within the casing upper portion and having a recess receiving the head and said lining including a lower portion received within the casing lower portion and having a recess seating the head, said lining lower portion being split into at least two portions surrounding the head,
   (d) the cup assembly including a generally hemispherical shell adapted to be cemented within the hip socket and adapted to receive the outer casing in rotatable relation.

6. A hip joint prosthesis as defined in claim 5, in which:
   (e) said shell includes a generally circular rim and a plurality of tabs project radially outward from said rim and adapted to engage a bone area surrounding the hip socket.

7. A hip-joint prosthesis adapted to connect a femur and a hip socket, the prosthesis comprising:
   (a) a stem assembly adapted to be attached to the femur and including a generally spherical head; and
   (b) a cup assembly including an outer casing adapted to be received within the socket and an inner lining receiving the head;
   (c) the cup assembly outer casing including an upper portion and a lower portion threadedly attached to the upper portion to encapsulate the lining and the lining including an upper portion received within the casing upper portion and having a recess receiving the head and said lining including a lower portion received within the casing lower portion and having a recess seating the head, said lining lower portion being split into at least two portions surrounding the head,
   (d) said lining upper portion including a lower generally conical surface and said lining lower portion including an upper conical portion operatively engagable with said lining upper conical portion.

8. A hip joint prosthesis adapted to connect a femur and a hip socket the prosthesis comprising:
   (a) a stem assembly adapted to be attached to the femur and including a generally spherical head; and
   (b) a cup assembly including an outer casing having an upper portion and a lower portion and adapted to be received within the socket and an inner lining receiving the head and having opposed lining portions, both lining portions being disposed between said upper and lower casing portions;
   (c) the cup assembly including resilient means therewithin disposed between said lining portions providing shock absorption between the head an the casing.

9. A hip joint prosthesis as defined in claim 8, in which:
   (d) said resilient means includes opposed plates having a spring means disposed therebetween.

10. A hip joint prosthesis as defined in claim 8, in which:
    (d) the resilient means includes a plurality of independent spring elements disposed between said lining portions.

11. A hip joint prosthesis adapted to connect a femur and a hip socket, the prosthesis comprising:
    (a) a stem assembly adapted to be attached to the femur and including a generally spherical head; and
    (b) a cup assembly including an outer casing adapted to be received within the socket and an inner lining receiving the head;
    (c) the cup assembly including resilient means therewithin providing the shock absorption between the head and the casing;
    (d) said lining including an upper portion and a lower portion, said upper portion having an insert block slidably receivable therewithin and the resilient means being disposed between said upper portion and said insert block.

12. A hip joint prosthesis adapted to connect a femur and a hip socket the prosthesis comprising:
    (a) a stem assembly adapted to be attached to the femur and including a generally spherical head; and
    (b) a cup assembly including an outer casing adapted to be received within the socket and an inner lining receiving the head and having opposed lining portions;
    (c) the cup assembly including resilient means therewithin disposed between said lining portions providing shock absorption between the head and the casing;
    (d) said resilient means including a opposed plates having a spring means disposed therebetween;
    (e) said spring means being provided by at least one wave washer, the wave washers being formed to accept a substantial amount of shock absorption resulting in increased longevity of the hip prosthesis.

13. A hip joint prosthesis adapted to connect a femur and a hip socket comprising:
    (a) a stem assembly adapted to be attached to a passage in the femur and including a generally spherical head; and (b) a cup assembly including an outer casing adapted to be received within the socket and an inner lining receiving the head;

(c) the stem assembly including an elongate stem and a shield and means between the stem and the shield permitting independent movement of the stem relative to the shield following insertion of the stem and shield together into the femur passage.

14. A hip joint prosthesis as defined in claim 13, in which:

(d) the stem includes a rear face having stepped attachment means and the shield includes a front face having cooperating stepped attachment means to control relative longitudinal movement between the stem and the shield.

15. A hip joint prosthesis as defined in claim 13, in which:

(d) the shield is adapted to be cemented within the femur and adjustable hose clamp means are adapted to be disposed about the femur to exert an inward pressure on said femur.

16. A hip joint prosthesis as defined in claim 13, in which:

(d) the shield is generally L-shaped and includes an elongate leg and a relatively short transverse leg.

17. A hip joint prosthesis as defined in claim 16 which:

(c) the elongate leg is perforated and adapted to receive cement from aligned cement-filled femur passages.

18. A hip joint prosthesis as defined in claim 16, which:

(e) the transverse leg is adapted to be engagable with the femuar and includes a hammerable surface.

19. A hip joint prosthesis adapted to connect a femur and a hip socket the prosthesis comprising:

(a) a stem assembly adapted to be attached to the femur and including a generally spherical head; and (b) a cup assembly including an outer casing adapted to be received within the socket and an inner lining receiving the head and having opposed lining portions;

(c) the cup assembly including resilient means therewithin disposed between said lining portions providing shock absorption between the head and the casing;

(d) the resilient means including at least one wave washer disposed between said lining portions.

20. A hip joint prosthesis adapted to connect a femur and a hip socket the prosthesis comprising:

(a) a stem assembly adapted to be attached to the femur and including a generally spherical head; and (b) a cup assembly including and outer casing adapted to be received within the socket and an inner lining receiving the head and having opposed lining portions;

(c) the cup assembly including resilient means therewithin disposed between said lining portions providing shock absorption between the head and the casing;

(d) the outer casing including and upper portion having a rim and a lower portion having a rim threadedly connected to the upper portion rim to encapsulate the lining.

* * * * *